Figure 1:
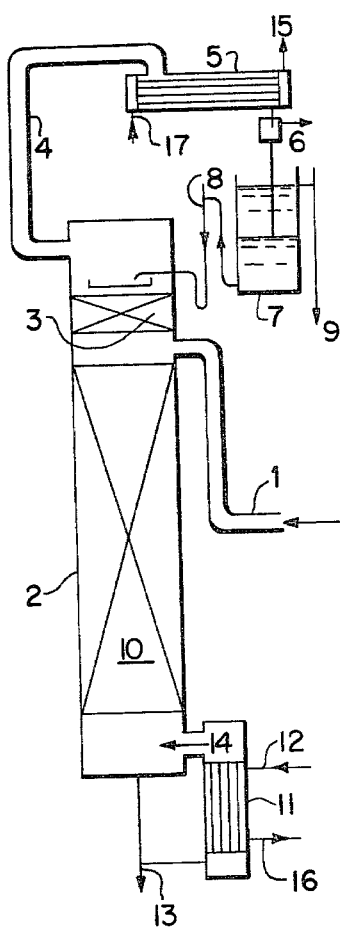

United States Patent [19]

Prahl

[11] 4,305,789
[45] Dec. 15, 1981

[54] ENERGY EFFICIENT PROCESS OF PREPARING TRIARYL PHOSPHATES

[76] Inventor: Walter H. Prahl, 400 - 64th Ave., Apt. 404W, St. Petersburg Beach, Fla. 33706

[21] Appl. No.: 127,504

[22] Filed: Mar. 5, 1980

[51] Int. Cl.$^3$ .............................................. B01D 3/14
[52] U.S. Cl. ...................................... 203/14; 203/25; 203/27; 203/DIG. 8; 260/978; 260/990
[58] Field of Search ................. 260/990, 978; 203/21, 203/25, 27, DIG. 8, 14

[56] References Cited

U.S. PATENT DOCUMENTS 2,805,240  9/1957  Prahl ................................... 260/990
3,945,891  3/1976  Aal et al. ............................. 260/990

Primary Examiner—Frank Sever
Attorney, Agent, or Firm—Sidney B. Ring; Hyman F. Glass

[57] ABSTRACT

In a process of preparing triaryl phosphates by direct esterification which comprises
A. Reaction Steps:
  The steps of
  (a) Reacting a hydroxyaryl with phosphoric acid or equivalent to form an aryl phosphate and water
  (b) Removing the water by entrainment by means of hydroxyaryl vapor, and
  (c) Condensing the water-containing entraining vapor, and
B. Dehydration Step:
  The step of separating the water from the water-containing entraining vapor by distillation, and
C. Recycling Steps:
  The steps of
  (a) Evaporating the dry hydroxyaryl liquid and
  (b) Using its vapor as the entraining vapor in step (A, b).

the improvement which comprises
  I. Carrying out the Reaction Steps A at essentially higher pressure than the Dehydration Step B, and
  II. Using all, or part of, the water-containing hydroxyaryl vapor from Step (A, b) as the heating medium in Step B.

5 Claims, 2 Drawing Figures

ENERGY EFFICIENT PROCESS OF PREPARING TRIARYL PHOSPHATES

This invention relates to the manufacture of aryl esters of phosphoric acid. More particularly, the present invention relates to an energy efficient improvement of the process for the manufacture of tri-aryl esters of orthophoric acid, such as tricresyl phosphate, by a direct method of esterification.

By the term "direct method of esterification" is meant a method of esterification which reacts a hydroxyaryl such as phenol, the cresols, xylenols, ethyl phenols, propyl phenols, etc. with phosphoric acid or equivalents in a reaction forming essentially only water as the byproduct, as opposed to the indirect method of producing aryl phosphates by reacting the hydroxyaryl with phosphorus oxychloride or similar phosphorous compounds, producing hydrogen chloride or similar compounds as byproduct.

The reaction of a hydroxyaryl with phosphoric acid or equivalent in the direct method of esterification can be visualized as progressing in three steps, forming the monophosphate by the reaction $OP(OH)_3 + ROH \rightleftarrows OP(OH)_2OR + H_2O$, then forming the di-phosphate by the reaction

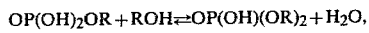

$OP(OH)_2OR + ROH \rightleftarrows OP(OH)(OR)_2 + H_2O,$ and then in the third step forming the tri-phosphate by the reaction

$OP(OH)(OR)_2 + ROH \rightleftarrows OP(OR)_3 + H_2O.$

The equilibrium concentration of water in the first step, and somewhat less so in the second step, is so that its removal poses no particular difficulties. In the third step, however, the equilibrium concentration of water is very low, and the removal of the water, a precondition for the progress of the reaction, requires special measures.

Such measures were disclosed in U.S. Pat. No. 2,805,240. According to that patent the water can be removed, and the reaction can be brought to, or close to, completion, by passing a large quantity of extremely dry hydroxyaryl vapor through the reaction mixture. According to said patent, the reaction can be carried out in batch or, preferably, in continuous operation. In either case a large quantity of moist (water-containing) hydroxyaryl vapor is produced, which has to be freed of its water content before it can be used to remove further quantities of water from the reaction mixture.

The present invention relates to an energy-efficient method of freeing such vapor of its water content.

The method of freeing the hydroxyaryl vapor, used for the removal or entrainment of water out of the reaction mixture, of the entrained water, as described in U.S. Pat. No. 2,805,240 or used in the practice of the invention disclosed in said patent, comprises the steps of (1) condensing the vapor, and (2) distilling the water off. As the next step (3) the residue of the distillation, essentially dry liquid hydroxyaryl, is evaporated, and the vapors are recycled to be used as the entraining vapor.

This conventional method of separating the entrained water from the entraining hydroxyaryl vapor requires a large quantity of energy. In step (1), condensing the vapor, its whole heat content is wastefully transferred to cooling water, from which in turn it has to be transferred to the environment. In step (2), distilling the water off, a similar quantity of energy, in form of high pressure steam or a high temperature heat transfer fluid, has to be added, in order to vaporize the moist hydroxyaryl liquid. This heat, also, is transferred at the top of the distilling column to cooling water and from there to the environment.

In former times this high consumption of energy would have been felt as a minor inconvenience of the otherwise technically and economically far superior process of direct esterification. With the present energy prices and environmental consciousness, however, the high amount of energy required in the drying of the entraining vapor represents a serious technical and economic problem to the direct esterification process.

Figure 2:
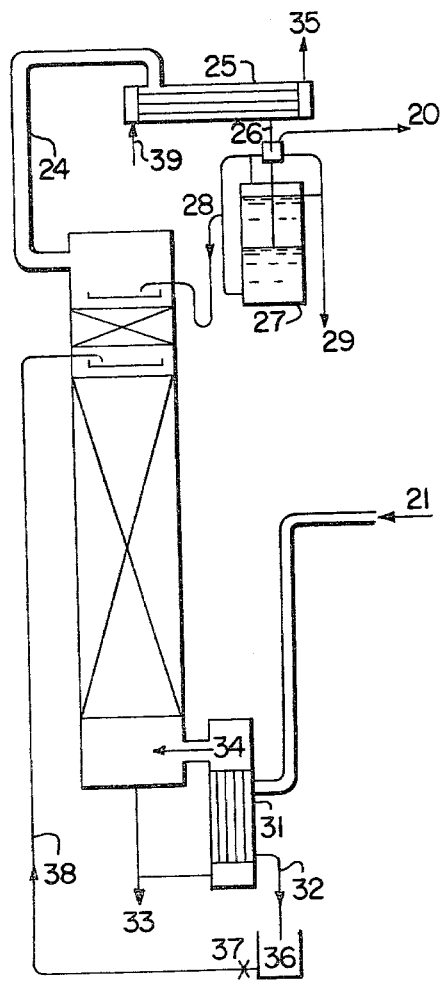

This invention will become more apparent upon considering the following description of the present invention taken in conjunction with the drawing wherein:

FIG. 1 is a diagrammatic illustration of apparatus for producing tri-aryl phosphates representing the prior art; and FIG. 2 is a diagrammatic illustration of apparatus for producing tri-aryl phosphate in accordance with the present invention.

This problem is solved, according to the present invention, by the combination of two steps, namely (I). Carrying out the esterification reaction at essentially higher pressure than the dehydrating distillation, and (II). Using the entraining vapor from the esterification reaction as heating medium for the dehydrating distillation. Thereby the process of U.S. Pat. No. 2,805,240 is improved as follows:

(1) The process of the present invention requires no external cooling medium, such as cooling water, for the condensation of the water-containing entraining vapor. None of the energy of the entraining vapor is wasted, none goes into the environment, and all of it is utilized.

(2) The process of the present invention requires no external energy for the distillation of the water-containing hydroxyaryl liquid. All the heat for that purpose is supplied by the condensation of the water-containing entraining vapor.

(3) As a consequence of (1) and (2) the equipment needed for carrying out a direct esterification according to the present invention is simplified in numerous respects: No condenser with its auxiliaries for the condensation of the entraining vapor, and no heat transfer fluid equipment for the distillation of the water-containing hydroxyaryl liquid with its auxiliaries is needed. The difference in pressure can be used for the transportation of liquids, saving the need for certain pumps.

(4) Operational advantages resulting from the combination of two different operations into one aggregate will be obvious to those skilled in the art.

Specific examples of hydroxyaryl compounds which may be converted into tri-aryl phosphates in accordance with the present invention include a wide variety of phenolic compounds including phenol; ortho-, meta-, and para-cresol; any of the six xylenols; any of the six tri-methyl phenols; any of the three tetra-methyl phenols; penta-methyl phenol; substituted phenols such as the ethyl, isopropyl, n-propyl, n-butyl, sec-butyl, tert-butyl, amyl, etc. which correspond to the series of methyl substituted phenols set forth above; phenols substituted with halogen, nitro- and similar groups; etc. Since the three hydrogens of ortho-phosphoric acid react independently of each other, they may be substituted by reaction with the same or two different or three different hydroxyaryl compounds. For example, the reaction product of phosphoric acid with a mixture of the three cresols contains the following compounds: o,o,o-cresyl phosphate, o,o,m-cresyl phosphate, o,o,p-cresyl phosphate, o,m,m-cresyl phosphate, o,m,p-cresyl phosphate, o,p,p-cresyl phosphate, m,m,m-cresyl phosphate, m,m,p-cresyl phosphate, m,p,p-cresyl phosphate and p,p,p-cresyl phosphate.

In order to facilitate understanding of the principles of this invention, and its advantages over the conventional method of drying the entraining vapor from a direct phosphoric acid esterification, the two methods will be compared in Example 1, describing the production of tri-phenyl-phosphate according to the conventional and to the method of the present invention.

Phenol was selected as hydroxyaryl for this example, because it poses more technical problems than most other hydroxyaryls, on account of the high mutual solubility of water and phenol, of the unusual and complicated vapor pressure relations between water and phenol, of the comparatively low boiling point of phenol, and of several other peculiarities of phenol, such as high solidification point, formation of a solid hydrate, etc. Having demonstrated by this example how to overcome those difficulties in the case of phenol, application of the principle of this invention to the production of other triaryl phosphates will be obvious to those skilled in the art.

EXAMPLE 1

The reactor system comprises five reactors arranged so that the liquid passes them in series in one direction while the vapor passes them countercurrently in the other direction. The reactors are kept at about 250° C. This type of reactor is shown in U.S. Pat. No. 2,805,240.

About 1000 kg/h of phosphoric acid, about 2000 kg/h of residue recycled from the recovery system and consisting mostly of diphenylphosphate, and about 3000 kg/h of phenol are continuously fed into the first reactor, while about 50,000 kg/h of essentially dry phenol vapor enter the last or fifth reactor. The reaction mixture leaving the fifth reactor and going to the recovery system comprises about 3300 kg/h triphenylphosphate, 2000 kg/h diphenylphosphate, some phenol and by-products. In the recovery system the product triphenylphosphate is separated from the residue. The latter is recycled to the reaction system.

The vapor leaving the first reactor comprises about 50,000 kg/h phenol and 555 kg/h water. The problem solved by the present invention is to separate by distillation this water from this phenol with consumption of a minimum of energy.

In order to demonstrate the advantage in energy consumption of the system according to the present invention over the conventional system, the energy required to dry the phenol in this example is calculated under (a) for the conventional, under (b) for my new system.

(a) Conventional System

The vapor from the reaction system, comprising about 50,000 kg/h phenol and about 555 kg/h water, enters the conventional drying system, schemetically represented in FIG. 1, through line 1 into column 2 with a temperature close to that of the reaction system, namely about 250° C. Its heat content serves to concentrate, in the upper section of the column the water content of the vapor phase from about 1.1% at the feed point to about 30% at the top of the column. It has, however, no effect upon the drying process in the lower section of the column. In order to bring the water content of the phenol down from about 1.1% to about 0.01% it has to be contacted with essentially dry phenol vapor generated in reboiler 11 and entering the column through duct 14.

The vapor pressure ratio $\alpha$ of water out of phenol is somewhat abnormal, dropping from a maximum of about 60 near $x=0.2$ to an approximately constant value of about 2.5 near $x=0.001$. (x designates the mole fraction of water in the liquid, y that in the vapor. $\alpha=y(1-x)/x(1-y)$). The bulk of the water entering the column through line 1, at an x of about 0.06 is thus easily removed by a few plates or transfer units immediately below the feed entrance 1, but the drying to the desired low value of about $x=0.0005$ is carried out in an area in which $\alpha$ is about 2.5. The maximum L/V ratio, corresponding to the concept of minimum reflux, is thus about 2.5. (L is the quantity of liquid passing down, V that of vapor passing up in the column during a given time.) Practically an L/V of about 2 is required. That makes the quantity of phenol vapor to be generated in reboiler 11 and entering the column through duct 14 into area 10, about equal to the quantity of feed. The energy required for that purpose enters 11 through line 12 in form of steam, or in any other suitable form. Condensate is withdrawn through duct 16 and essentially pure phenol is withdrawn through duct 13.

The vapor leaving the top of the column passes through duct 4 into condenser 5, where it is condensed and cooled to the lowest temperature economically obtainable with the available cooling medium, for instance to 25° C., dissipating its energy content to the cooling water or air. Cooling fluid enters through 17 and discharges through 15. The condensate passes through line 6 into separator 7, where it separates into an aqueous layer comprising about 550 kg/h water saturated with about 50 kg/h of phenol, which passes through line 9 to environmental treatment, and an organic layer which passes through line 8 which is essentially phenol saturated with water at the prevailing temperature. At about 25° C. it contains about 29% water. This layer returns through line 8 into area 3 of column 2.

The detailed operation of this conventional drying system is given in the Material- and Energy-Balance of Table 2.

The individual Enthalpies used in deriving the energy balance are given in Table 1.

TABLE 1

| Enthalpies of water and phenol, in Joule/kilogram. Basis: Liquid 0° C. = 0.0000 J/Kg. | | | | |
|---|---|---|---|---|
| Temperature | Water | | Phenol | |
| °C. | Liquid | Vapor | Liquid | Vapor |
| 0° | 0.0000 | | 0.0000 | |
| 25° | 1.0477 E05 | 2.5473 E06 | 5.106 E04 | 6.479 E05 |
| 63° | 2.6365 E05 | 2.6149 E06 | 1.337 E04 | 7.067 E05 |
| 104° | 4.3595 E05 | 2.6821 E06 | 2.297 E04 | 7.731 E05 |
| 130° | 5.4632 E05 | 2.7198 E06 | 2.942 E04 | 8.189 E05 |
| 182° | 7.7195 E05 | 2.7780 E06 | 4.317 E04 | 9.189 E05 |
| 250° | 1.0859 E06 | 2.8003 E06 | | 1.060 E06 |

(b) A Dehydration System according to the Present Invention

A drying system according to the present invention is schematically represented by FIG. 2.

The essential difference in operating pressure between the reaction- and the dehydration-system, characteristic of, and required according to, the present invention is, in this case, achieved by operating the reaction system at atmospheric pressure, while the dehydration system, by connection to a vacuum pump through line 20, is kept at a pressure of about 1.9 E 0.4 Pa.(About 142.5 mm Hg).

The superheated mixture of phenol- and water-vapor coming from the reaction system with the same temperature, composition and quantity as under (a) enters through line 21 of the reboiler 31 as heating medium. By heat exchange with the phenol boiling on the other side of the heat transfer surface at approximately 130° C. it is cooled, and condensed. Depending upon circumstances the condensate may be cooled below its boiling point of 182° C. That, however, does not influence the energy balance of the system, because the condensate returns, through line 32, holding tank 36, control valve 37, and line 38 into the column, so that the total energy content of the material in line 21 enters the system regardless of its partition between lines 34 and 38. For the energy balance it was assumed that no subcooling takes place.

The condensate entering the column through line 38 passes down the column in countercurrent to the ascending vapor, entering the column through duct 34, generated in reboiler 31, and is thus essentially freed of water. The essentially dry phenol leaves the system through line 33, and is recycled to the reaction system. The mixture of phenol and water-vapor passes from the column through line 24 to condenser 25. Cooling fluid enters through 39 and discharges through 35. The vapor leaving the top of the column passes through duct 24 into condenser 25. Condensate passes through line 26 into separator 27 where it separates into an aqueous layer removed at line 29 and an organic layer which passes through line 28.

The material- and energy-balance of this system is given in Table 3.

Comparison of Table 3 with Table 2 shows that for an equal quantity of starting material and product:

requires supply of about 2.43 E10 J/h (line 12), equal to about $23\times 10^6$ BTU/h, and equivalent to about 35,000 lbs/h of high pressure steam.

2. The system of the present invention removes in the condenser about 4.0 E10 J/h of heat, equivalent to about 1000 gal/min cooling tower water, while the conventional system dissipates about 1.7 E10 J/h more (line 15), consuming about 40% more cooling water.

3. The conventional system has in the lower, most critical, section of the column an L/V ratio of about 2.0, while the system according to the present invention has an L/V of about 1.8. (Line 33 plus line 34, divided by line 34). It therefore achieves the same drying effect with fewer plates or transfer units in the lower section of the column than required in the conventional system, or, for a given number of plates, it achieves a correspondingly higher degree of dryness.

4. By judicious use of gravity flow and movement of material by utilizing the pressure differential, the necessity of pumps and other mechanical devices for moving materials is obviated, thereby saving the energy of their operation and the cost of their maintenance. The only energy-consuming device is the vacuum pump.

5. Other advantages, of a less obvious nature, will be apparent to those skilled in the art.

The numerical and quantitative advantages of the present invention have been demonstrated by the above illustrative examples.

Triarylphosphates find their main use as fire-retardant plasticisers for poly-vinylchloride and similar plastics. The lower esters, namely triphenyl- and tricresyl-phosphates, are preferred for this purpose, but esters of hydroxyaryls of higher molecular weight, including those of naphthols, have many other uses.

One of the characteristics of this invention is the essential difference in pressure between the reaction and dehydration or drying system. Essential difference in this connection means a difference large enough to make it technically and economically feasible to use the hydroxyaryl vapor from the reaction system as heating medium for the evporation of the same hydroxyaryl in the drying system. In the case of phenol, in the example, the essential difference was achieved by operating the reaction system under atmospheric pressure, and the drying system under a reduced pressure of about 1.9 E04 (about 142.5 mm Hg). Under this pressure the dry phenol in the reboiler boils at slightly above (on account

TABLE 2

| | | Material- and Energy-Balance. Conventional System | | | | | | | |
|---|---|---|---|---|---|---|---|---|---|
| Line | | 1 | 4 | 8 | 9 | 12 | 13 | 14 | 15 |
| State | | vapor | vapor | Liquid | Liquid | | liquid | vapor | |
| Temperature °C. | | 250° | 104° | 25 | 25 | | 182 | 182 | — |
| Quantity kg/h | phenol | 50000 | 31502 | 31452 | 50 | — | 49950 | 49950 | — |
| | water | 555 | 13396 | 12846 | 550 | — | 5 | 5 | — |
| | total | 50555 | 44898 | 44298 | 600 | — | 49955 | 49955 | |
| Enthalpy J/h | | 5.4554 E10 | 6.0284 E10 | 2.9518 E09 | 6.0177 E07 | 2.4346 E10 | 2.1567 E10 | 4.5913 E10 | 5.7272 E10 |

TABLE 3

| | | Material- and Energy-Balance. Present Invention. | | | | | | | |
|---|---|---|---|---|---|---|---|---|---|
| Line | | 21 | 24 | 28 | 29 | 32 | 33 | 34 | 35 |
| State | | vapor | vapor | liquid | liquid | liquid | liquid | vapor | |
| Temperature °C. | | 250 | 63 | 25 | 25 | 182 | 130 | 130° | |
| Quantity, kg/h | phenol | 50000 | 22884 | 22834 | 50 | 50000 | 49950 | 61992 | |
| | water | 555 | 9877 | 9327 | 550 | 555 | 5 | 6 | |
| | total | 50555 | 32761 | 32161 | 600 | 50555 | 49955 | 61998 | |
| Enthalpy J/h | | 5.4554 E10 | 4.1999 E10 | 2.1431 E09 | 6.0177 E07 | 2.2013 E10 | 1.4698 E10 | 5.0782 E10 | 3.9796 E10 |

1. The system of the present invention requires no supply of external heat, while the conventional system of the pressure drop in the column) 130° C. The moist phenol from the reactor system has an average condensation temperature at atmospheric pressure of about 178° C. (Boiling point of dry phenol: 181.75° C.). The temperature difference of about 178°−130°=48° C. is entirely within the technical and economic range for a reboiler, even though its surface would be slightly larger than for operation with steam.

The average condensation temperature of the vapor at the top of the column, containing about 33% water, is about 63° C. Even cooling tower water in a warm climate would be cold enough to achieve condensation in a condenser of moderate, technically and economically entirely acceptable size.

While this pressure difference, and the way it is produced, is believed to be optimal under normal conditions, other arrangements are entirely within the scope of this invention. For instance, it would be entirely feasible to operate the reaction system under a pressure of, for instance, 2+05 Pa (about 1501 mm Hg), and operate the drying system at atmospheric pressure. The reaction temperature would have to be raised, for instance to 280° C., but for phenol such reaction temperature is entirely acceptable, while it might be too high for more sensitive hydroxyaryls. The moist vapor from the reactor would then have an average condensation temperature of about 204° C. (Boiling point of dry phenol at this pressure is about 208° C.). The boiling point of the dry phenol in the drying system would then be slighly above 181.75° C. The temperature difference of about 22° C. is not too small for a practical reboiler. The condenser operating at about 103° C. would pose no problem.

Although it is convenient to operate one of the systems at atmospheric pressure, there is no necessity to do so. It is entirely practical to operate both systems at higher, or at lower, than atmospheric pressure, or operate one above, one below atmospheric pressure. The only condition is that the difference is large enough to permit technically and economically practical use of the vapor from the reaction system as heating medium in the vaporization of the reactant hydroxyaryl compound in the drying system.

It is also within the scope of this invention to use only part of the vapor from the reaction system as heating medium for the vaporization of hydroxyaryl in the drying system. For instance, as pointed out in the example, the arrangement described there provides more vapor passing upward in the drying column, than provided for in the conventional arrangement, thereby giving a better drying effect. In case the drying effect of the conventional arrangement is satisfactory, the same effect can be achieved by using only part of the vapor from the reaction system as heating medium in the drying system. The energy in the rest of the vapor can then be utilized otherwise, for instance for generating low pressure steam.

I claim:
1. A process for the production of triarylphosphates by the direct esterification of an hydroxyaryl and phosphoric acid characterized by
   I. Removing the water formed in the esterification reaction by entraining said water with an hydroxyaryl vapor,
   II. Dehydrating the water-containing hydroxyaryl vapor by distillation at an essentially lower pressure than used in the esterification reaction, and
   III. Passing at least a portion of the entraining vapor from I, in indirect heat exchange with a reboiler of the distillation in II.
2. The process of claim 1, wherein the entrained water and hydroxyaryl vapor from the esterification reaction condenses due to said heat exchange, and said condensate is fed into the top portion of said column as reflux.
3. The process of claim 2, wherein vapors exit the top of said column and flow to a condenser, wherein at least partial condensation of said vapors takes place, and at least a portion of the resultant condensate is returned to the column, as reflux, at a point above the entry of said prior recited reflux.
4. The process of claim 3, wherein the distillation column is operated under vacuum and the esterification takes place at atmospheric pressure.
5. The process of claim 4, wherein relatively dry hydroxyaryl is withdrawn from the distillation column and is recycled for esterification.

* * * * *